United States Patent
Kim et al.

(10) Patent No.: US 7,880,023 B2
(45) Date of Patent: *Feb. 1, 2011

(54) 2-NITRATOETHYL OXIRANE, POLY (2-NITRATOETHYL OXIRANE) AND PREPARATION METHOD THEREOF

(75) Inventors: Jin Seuk Kim, Daejeon (KR); Jin Rai Cho, Daejeon (KR); Keun Deuk Lee, Daejeon (KR); Jeong-Kook Kim, Daejeon (KR)

(73) Assignee: Agency for Defense Development A Non Profit Korean Organization, Yoosung Daejon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/431,754

(22) Filed: Apr. 28, 2009

(65) Prior Publication Data

US 2009/0275765 A1    Nov. 5, 2009

Related U.S. Application Data

(63) Continuation of application No. 11/879,016, filed on Jul. 12, 2007, now abandoned.

(30) Foreign Application Priority Data

Apr. 30, 2003    (KR)    ...................... 10-2003-0027805

(51) Int. Cl.
*C07D 303/08*    (2006.01)
(52) U.S. Cl. ...................... 549/551; 549/518
(58) Field of Classification Search ................ 549/551, 549/518
See application file for complete search history.

Primary Examiner—Janet L Andres
Assistant Examiner—David E Gallis
(74) Attorney, Agent, or Firm—Jeffrey J. King; Patent Networks Law Group PLLC

(57) ABSTRACT

A synthesis of an energetic prepolymer used as a high-energy binder for an insensitive and high performance explosive is disclosed. More specifically, provided are a novel compound 2-nitratoethyl oxirane expressed by formula III, a novel compound poly(2-nitratoethyl oxirane) expressed by formula IV, obtained by polymerization of 2-nitratoethyl oxirane used as a monomer and a preparation method thereof. The compound, used as an energetic prepolymer and a monomer for preparation thereof can substitute for existing poly(glycidyl nitrate) (PGN) which has been known to be a promising one having the best performance among existing energetic prepolymers, but which has a problem to be self-decomposed after synthesis of polyurethane elastomer, to solve this problem.

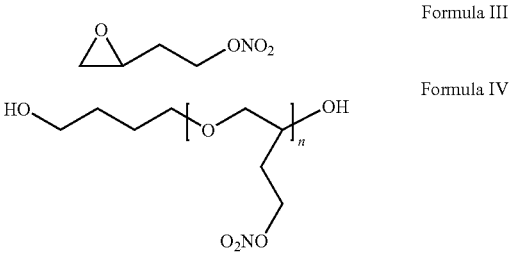

n = 10~40

1 Claim, No Drawings

2-NITRATOETHYL OXIRANE, POLY (2-NITRATOETHYL OXIRANE) AND PREPARATION METHOD THEREOF

CROSS REFERENCE TO RELATED APPLICATIONS

This application is a CONTINUATION of DIVISIONAL application Ser. No. 11/879,016, filed Jul. 12, 2007 now abandoned, which claims priority right of U.S. patent application Ser. No. 10/830,972, filed Apr. 22, 2004 (issued Oct. 30, 2007 as U.S. Pat. No. 7,288,681), which is entitled to priority of REPUBLIC OF KOREA patent application 27805/2003, filed Apr. 30, 2003.

BACKGROUND OF THE INVENTION

1. Field of the Invention

The present invention relates to a synthesis of an energetic prepolymer used as a high-energy binder for an insensitive and high performance explosive.

2. Description of the Background Art

Currently, HTPB (Hydroxyl-Terminated Polybutadiene), a prepolymer for a binder for Plastic-Bonded Explosives (FBX's) is being widely used as a binder for polyurethane groups. This binder is included in PBX in the amount of about 15% to improve mechanical properties of PBX's. However, this binder is, an inert material, and thereby causing reduction of energy of PBX's. Therefore, many efforts are made to develop a high-energy contained binder (an energetic binder) for increasing the energy of PBX's. Among energetic binders developed as a result of such efforts, poly(glycidyl nitrate) (PGN) expressed as the following formula 1 is a representative one. A monomer structure of the PGN is shown in following formula 2.

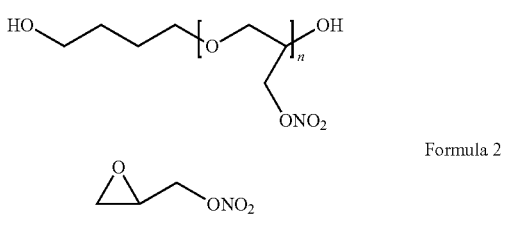

Formula 2 n = 10 ~ 40

However, as shown in following reaction scheme 1, after a polyurethane elastomer has been synthesized, the PGN of Formula 1 is self-decomposed in the polyurethane elastomer.

Reaction Scheme 1

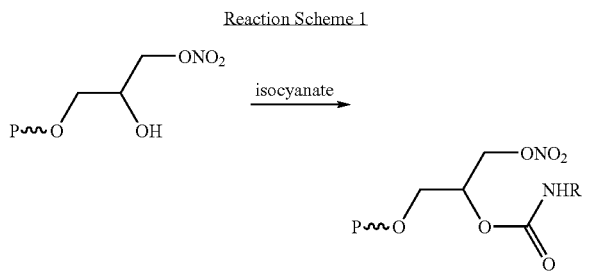

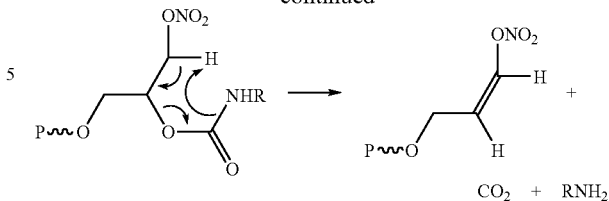

As shown in reaction scheme 1, when the polyurethane elastomer is synthesized by using the PGN of Formula 1, hydrogen bonding to carbon to which a nitrate group bonds is chemically acidified thus to easily cause a decomposition reaction as shown in reaction scheme 1 thereby causing a decomposition of the main chain of polyurethane. Nevertheless, since the PGN has been known as a material having the best performance among existing energetic prepolymers, many researches are made in order to solve such problems. However, outstanding results have not been obtained yet.

SUMMARY OF THE INVENTION

Therefore, an object of the present invention is to provide a monomer, 2-nitratoethyl oxirane expressed as formula III, which has energy equal to PGN and an excellent storage stability, and poly(2-nitratoethyl oxirane) expressed as formula IV, which is polymerized therefrom.

The foregoing and other objects, features, aspects and advantages of the present invention will become more apparent from the following detailed description of the present invention when taken in conjunction with the accompanying drawings.

DETAILED DESCRIPTION OF THE PREFERRED EMBODIMENTS

Reference will now be made in detail to the preferred embodiments of the present invention, examples of which are illustrated in the accompanying drawings.

The present invention relates to a synthesis of an energetic prepolymer used as a high-energy binder for an insensitive and high performance explosive. More particularly, the present invention provides a novel compound, 2-nitratoethyl oxirane expressed as formula III and poly(2-nitratoethyl oxirane) expressed as formula IV, which is polymerized therefrom.

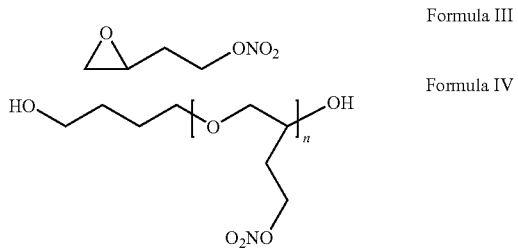

n = 10~40

2-nitratoethyl oxirane of formula III is used as a monomer for a synthesis of poly(2-nitratoethyl oxirane) of formula IV. In addition, poly(2-nitratoethyl oxirane) of formula IV has a chemical structure similar to the PGN of formula 1 which is a prepolymer conventionally used as a high energy binder, and also shows performance as a high-energetic prepolymer similar to the PGN. As shown in reaction scheme 1, the existing PGN is self-decomposed since hydrogen bonding to carbon to which a nitrate group bonds is unstable and a urethane group attacks the unstable hydrogen, thereby being rearranged. However, unlike the existing PGN, as shown in following reaction scheme 2, the compound IV in accordance with the present invention includes one more methylene group, whereby the unstable hydrogen is not spatially attacked by the polyurethane group, and thus the compound IV is not self-decomposed in a polyurethane elastomer. Accordingly, the compound IV is very useful as a high-energetic prepolymer capable of solving the problem in using the PGN.

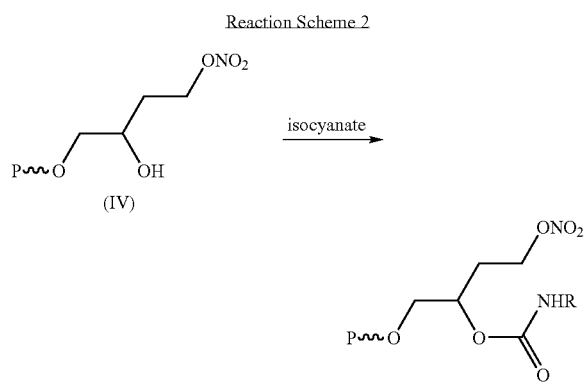

A synthesis of 2-nitraoethyl oxirane of formula III and a synthesis process of poly(2-nitraoethyl oxirane) of formula IV are shown in following reaction scheme 3.

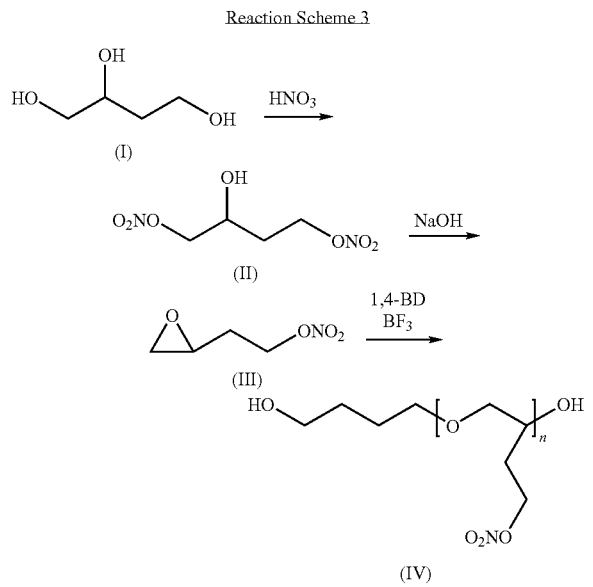

Said reaction scheme will now be explained in more detail.

First, nitric acid is added to 1,2,4-butanetriol of the formula I and reacted at a room temperature. The reaction mixture is extracted with methylene chloride (MC), washed with water and dried. The solvent is removed to obtain 1,4-dinitrato-2-butanol of formula II (reaction scheme 3-1).

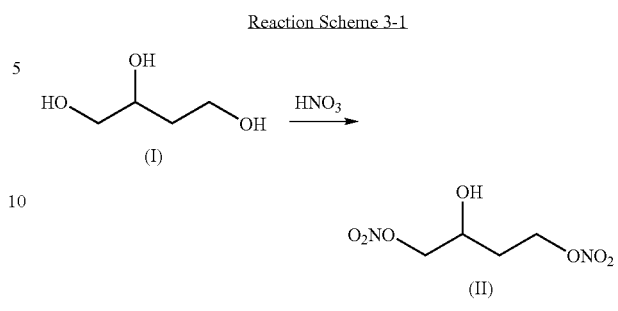

Then, sodium hydroxide is added to the obtained 1,4-dinitrato-2-butanol and reacted. The reaction mixture is extracted with MC, washed with water and dried. The solvent is removed, to obtain 2-nitratoethyl oxirane of formula III (reaction scheme 3-2).

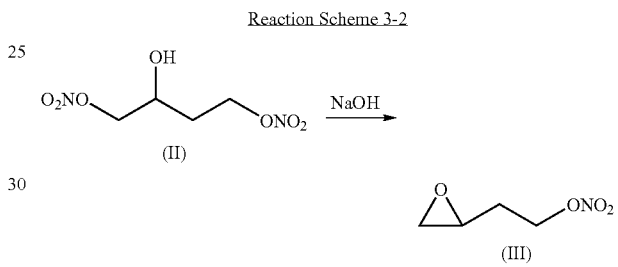

Then, boron trifluoride ($BF_3$) and 1,4-butandiol are reacted to the obtained 2-nitraoethyl oxirane of formula III and the polymerization thereof is performed to obtain poly(2-nitraoethyl oxirane) of formula IV (reaction scheme 3-3).

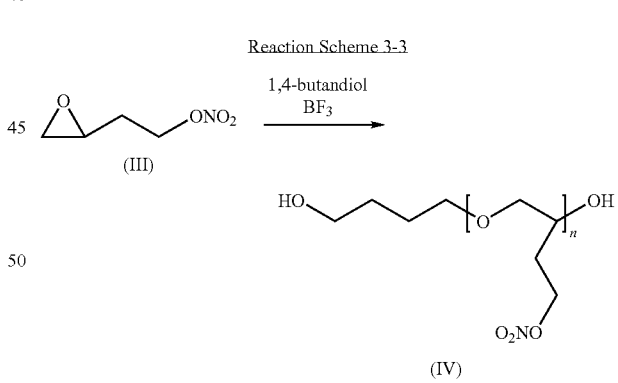

The obtained poly(2-nitratoethyle oxirane) is equal to PGN, an existing energetic prepolymer, in an energy aspect but is not self-decomposed, which has been pointed out as a problem of the PGN. Accordingly, poly(2-nitratoethyl oxirane) is a very useful material as a new energetic prepolymer which is used as a high energy binder for an insensitive and high performance explosive.

Hereinafter, the present invention will be described in more detail with reference to examples. However, the present invention is not limited by the following examples.

Example 1

Synthesis of 1,4-dinitrato-2-butanol 31.8 g (0.3 mol) of 1,2,4-butanetriol of formula I was put in a 3-neck flask of 250 ml equipped with a thermometer, a reflux condenser and a dropping funnel, and the temperature was controlled to be 0° C. or below. 100.2 g (1.59 mol) of 98% nitric acid was put in the dropping funnel, and the nitric acid was dropped to a solution, controlling the temperature of the reaction solution so as not to be over 10° C. After the nitric acid had been all dropped, the reaction mixture was left at a room temperature for about one hour to complete the reaction. Then, the obtained reaction solution was slowly added to 150 ml of ice water.

The reaction mixture was extracted with 100 ml of methylene chloride. Then, the resulting material was washed three times with 150 ml of 10% sodium hydrogen carbonate, washed twice with 150 ml of a sodium chloride saturated solution, and dehydrated with anhydrous magnesium sulfate. Then, the solid was removed by filtering the solution, and volatile matter was removed by evacuating the solution for five hours at 10 mmHg/60° C., to obtain 39.9 g of 1,4-dinitrato-2-butanol (yield: 70%).

NMR (CDCl$_3$, δ for TMS): 4.40, 4.20 (m, 2H), 4.06 (m, 1H), 2.50, 2.19 (m, 2H)

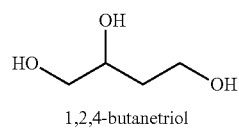

1,2,4-butanetriol

Formula I

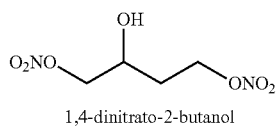

1,4-dinitrato-2-butanol

Formula II

Example 2

Synthesis of 2-nitratoethyl oxirane 9.9 g (0.205 mol) of 1,4-dinitrato-2-butanol obtained in example 1 was put in a 250 ml 3-neck flask and distilled water was added thereto. The temperature of a reaction solution was controlled to be 10° C. or below, then 24.6 g (0.306 mol) of 50% sodium hydroxide was injected thereto using a dropping funnel, controlling the temperature of the reaction solution so as not to be over 10° C. After the injection, a reaction was additionally made for three hours at a room temperature and completed.

Then, the reaction solution was extracted three times with 60 ml of methylene chloride. The resulting material was washed twice with 150 ml of sodium chloride saturated solution, and dehydrated with anhydrous magnesium sulfate. The obtained solution was filtered to remove the solid and then evacuated for five hours at 10 mmHg/60□ to completely remove volatile matter. In order to obtain pure 2-nitratoethyl oxirane which could be polymerized to a prepolymer, the resulting product was purified using a Kuqelrohr distillation apparatus (Aldrich, Z40, 11405) to obtain 14.2 g of pure 2-nitratoethyl oxirane of formula III (yield: 52%).

NMR (CDCl$_3$, δ for TMS): 4.58 (t, 2H), 3.00 (m, 1H), 2.61, 2.53 (m, 2H), 2.03, 1.85 (m, 2H)

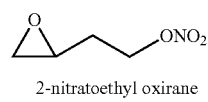

2-nitratoethyl oxirane

Formula III

Example 3

Synthesis of poly(2-nitratoethyl oxirane)

0.18 g (2 mol) of 1,4-butandiol was added to 0.28 g (2 mol) of boron trifluoride etherate (BF$_3$OEt$_2$) and evacuated for about two hours to completely remove ether. Then, 10 ml of methylene chloride was added thereto. A solution of 6.65 g (50 mol) of 2-nitratoethyl oxirane obtained in example 2 dissolved in methylene chloride was injected to the resulting solution for about three hours to perform polymerization. After polymerization, 50 ml of water and 30 ml of methylene chloride were additionally put therein for washing. Then, the resulting material was washed twice with 50 ml of saturated sodium chloride solution and dehydrated with anhydrous magnesium sulfate. 20 ml of ethanol was added to the obtained polymer and stirred to wash non-reaction organic matter. Then, volatile matter was completely removed by evacuating the resulting material for five hours at 1 mmHg/80□ to obtain polymer poly(2-nitratoethyl oxirane) expressed by formula IV.

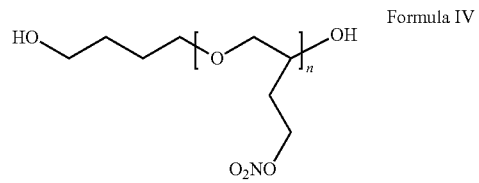

poly(2-nitratoethyl oxirane)

n = 10~40

Formula IV

A yield of the obtained polymer was approximately 91%, a numeric average of the molecular weight 2, 380, a polydispersity 1.18, a hydroxyl group 0.586 eq/kg, a glass transition temperature −43° C., and a thermal decomposition onset temperature 180° C.

Example 4

Hardness Change of poly(2-nitratoethyl oxirane) Group Polyurethane Elastomer After synthesizing a polyurethane elastomer with each of poly(2-nitratoethyl oxirane) obtained in a manner described in example 3 and existing poly(glycidyl nitrate) (PGN) by using N-100 curing agent, a change of hardness (Shore D hardness) was examined and the result was shown in the following table 1.

TABLE 1

Changes of hardness (shore D hardness) of
polyurethane elastomer formed by using poly(2-nitratoethyl oxirane)
and existing PGN over time

| | \multicolumn{8}{c|}{time} |
| | 3 days | 5 days | 7 days | 10 days | 15 days | 30 days | 3 months | 6 months |
|---|---|---|---|---|---|---|---|---|
| poly(2-nitratoethyl oxirane) | 2.0 | 3.0 | 3.5 | 3.5 | 3.5 | 3.5 | 3.6 | 3.6 |
| PGN | 2.0 | 3.0 | 2.5 | completely decomposed | — | — | — | — |

As shown in Table 1, in case of polyurethane elastomer formed by using an existing PGN, a polymer began decomposed from solid of gum-stock to liquid after about 1 week. However, in case of polyurethane elastomer formed by using poly(2-nitratoethyl oxirane) in accordance with the present invention, a physical property was maintained even after 6 months.

The compound of the present invention, used as an energetic prepolymer or a monomer for preparation thereof can substitute for existing poly(glycidyl nitrate) (PGN) which has been known to be a promising one having the best performance among existing energetic prepolymers, but which has a problem to be self-decomposed after the synthesis of polyurethane elastomer, to solve this problem.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A method for preparing 2-nitratoethyl oxirane expressed by formula III.

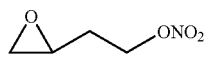

Formula III comprising the steps of:
reacting 1,2,4-butanetriol with nitric acid to obtain 1,4-dinitrato-2-butanol; and
treating the 1,4-dinitrato-2-butanol with sodium hydroxide to obtain 2-nitratoethyl oxirane.

* * * * *